(12) United States Patent
Wilmes

(10) Patent No.: US 9,382,046 B2
(45) Date of Patent: Jul. 5, 2016

(54) CLOSURE SYSTEM FOR REAGENT VESSEL RECEIVING POSITIONS IN AN AUTOMATIC ANALYSIS APPARATUS

(71) Applicant: Siemens Healthcare Diagnostics Products GmbH, Marburg (DE)

(72) Inventor: Hugo Wilmes, Bad Soden (DE)

(73) Assignee: Siemens Healthcare Diagnostics Products GmBH, Marburg (DE)

( * ) Notice: Subject to any disclaimer, the term of this patent is extended or adjusted under 35 U.S.C. 154(b) by 176 days.

(21) Appl. No.: 14/196,267

(22) Filed: Mar. 4, 2014

(65) Prior Publication Data
US 2014/0271403 A1 Sep. 18, 2014

(30) Foreign Application Priority Data
Mar. 18, 2013 (EP) .................................. 13159671

(51) Int. Cl.
| | |
|---|---|
| *B65D 43/26* | (2006.01) |
| *B01L 9/06* | (2006.01) |
| *G01N 35/02* | (2006.01) |
| *B01L 3/00* | (2006.01) |
| *G01N 35/00* | (2006.01) |
| *G01N 35/04* | (2006.01) |

(52) U.S. Cl.
CPC ............... *B65D 43/265* (2013.01); *B01L 3/523* (2013.01); *G01N 35/025* (2013.01); *B01L 3/50825* (2013.01); *B01L 9/06* (2013.01); *G01N 2035/00287* (2013.01); *G01N 2035/0405* (2013.01)

(58) Field of Classification Search
None
See application file for complete search history.

(56) References Cited

U.S. PATENT DOCUMENTS

| | | | | |
|---|---|---|---|---|
| 4,841,818 A | | 6/1989 | Plapp et al. | |
| 5,271,897 A | * | 12/1993 | Wurschum | B01L 3/50853 422/561 |
| 5,578,494 A | * | 11/1996 | Clark | B01F 11/0022 215/235 |
| 5,628,962 A | * | 5/1997 | Kanbara | B01L 99/00 215/235 |
| 6,531,096 B1 | * | 3/2003 | Deveney | B65B 69/00 422/549 |
| 6,866,820 B1 | | 3/2005 | Otto et al. | |
| 2010/0080732 A1 | * | 4/2010 | Mototsu | B01L 3/50825 422/63 |
| 2013/0064735 A1 | * | 3/2013 | Arras | B01L 3/523 422/430 |
| 2013/0118118 A1 | * | 5/2013 | Kubler | B01L 3/50825 53/381.1 |

FOREIGN PATENT DOCUMENTS

| | | |
|---|---|---|
| DE | 10026099 | 11/2001 |
| DE | 102010029136 | 11/2011 |
| EP | 0523425 | 1/1993 |
| FR | 2734241 | 11/1996 |
| GB | 2269583 | 2/1994 |
| GB | 2269809 | 2/1994 |

\* cited by examiner

*Primary Examiner* — Jill Warden
*Assistant Examiner* — Benjamin Whatley
(74) *Attorney, Agent, or Firm* — Dugan & Dugan, PC

(57) ABSTRACT

A closure system for a holder for a reaction vessel in an automatic analysis apparatus includes a lid secured movably on a retainer element, wherein the lid closes an opening of the holder in a closed position and opens the opening of the holder in an open position. The closure system further includes a restoring element configured to, depending on the position of the lid, exert a restoring force in the direction of the closed position or of the open position.

17 Claims, 4 Drawing Sheets

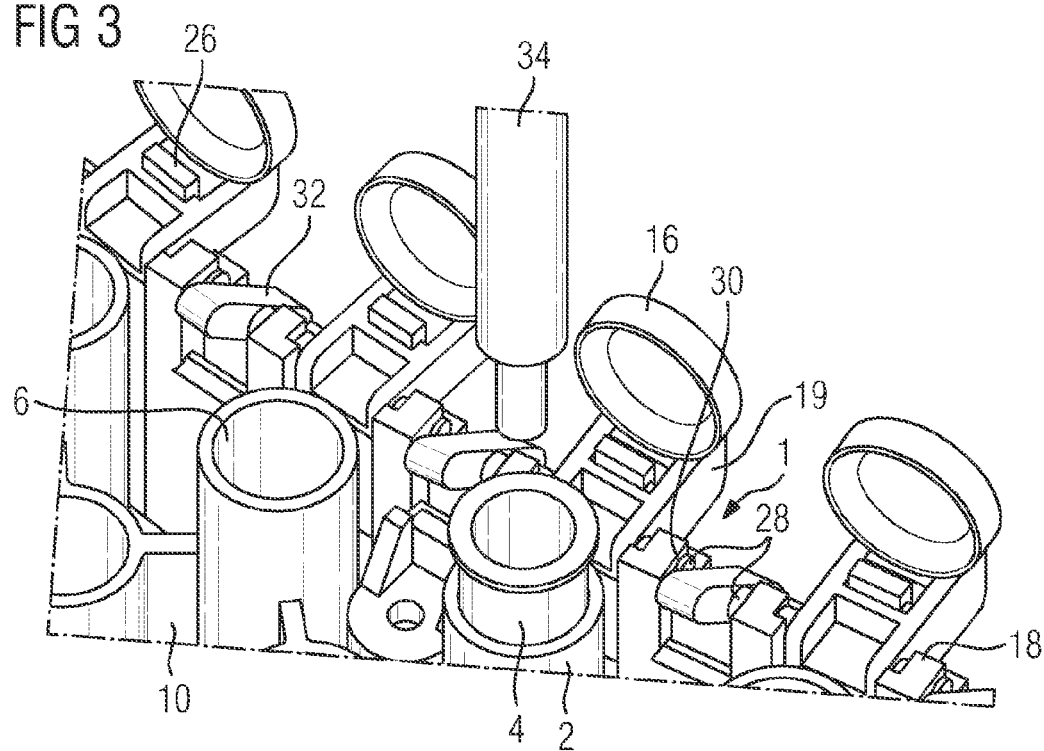
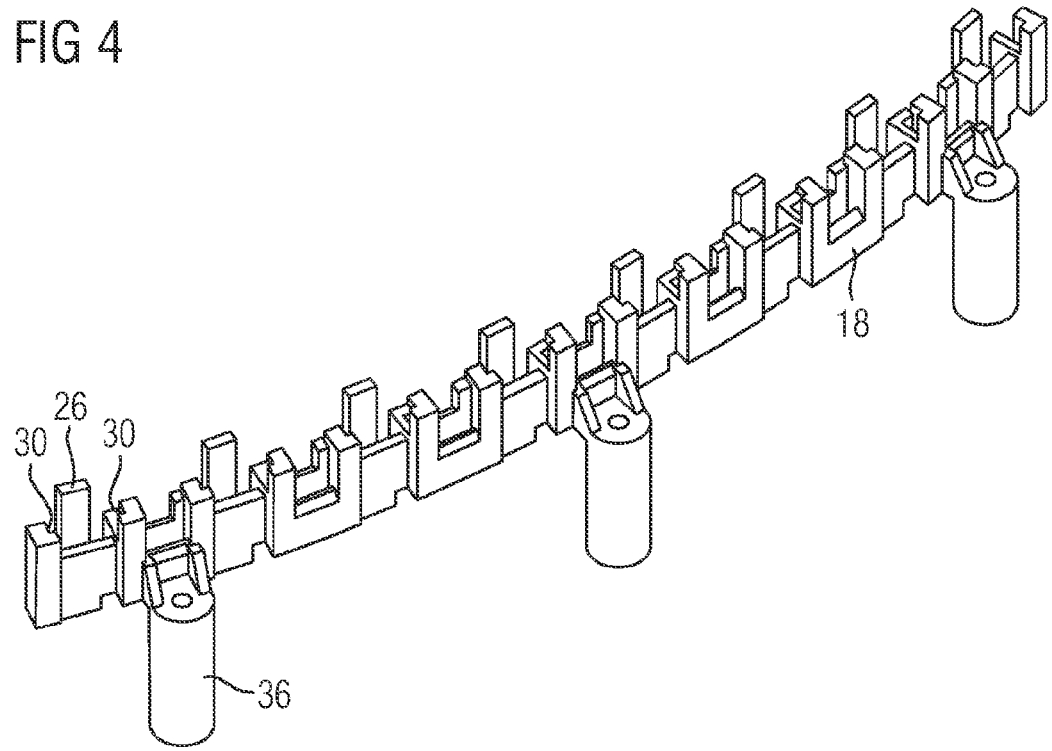

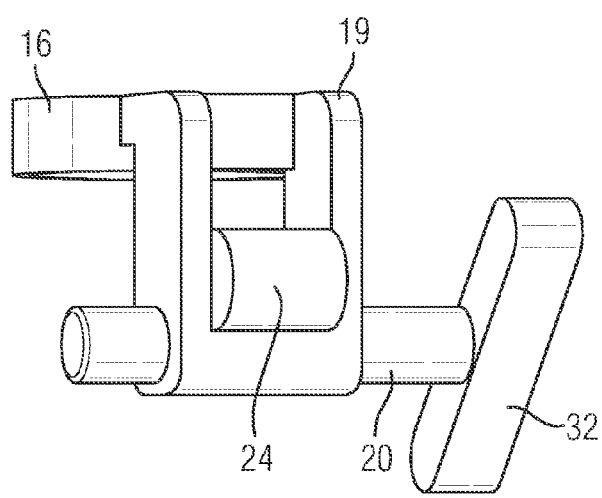

CLOSURE SYSTEM FOR REAGENT VESSEL RECEIVING POSITIONS IN AN AUTOMATIC ANALYSIS APPARATUS

FIELD

The invention relates to a closure system for a holder for a reaction vessel in an automatic analysis apparatus.

BACKGROUND

Numerous detection and analysis methods for determining physiological parameters in samples of bodily fluid such as blood, plasma, serum or urine or in other biological samples are nowadays carried out in an automated manner in corresponding analysis apparatus.

Current analysis apparatus are able to carry out many different kinds of detection reactions and analyses with a large number of samples. Analysis apparatus of the kind presently used in clinical laboratories or in blood banks usually comprise an area for the delivery of sample vessels that contain the primary samples to be analyzed. To feed the sample vessels into the analysis apparatus, a transport system is usually provided which firstly transports the sample vessels to a sample identification device, which detects sample-specific information applied to a sample vessel and transmits said information to a storage unit. Thereafter, the sample vessels are transported to a sampling station. With the aid of a sample pipetting device, at least one aliquot of the sample liquid is removed there from a sample vessel and is transferred to a reaction vessel.

The reaction vessels are generally in the form of disposable cuvettes which are stored in a cuvette container in the analysis apparatus and which are transferred automatically from the storage container to defined receiving positions. The reagents needed for providing different types of test-specific reaction mixtures are located in reagent containers, which are stored in a reagent station. The reagent containers are delivered to the analysis apparatus either automatically or manually.

Measurement systems which are based on photometric (e.g. turbidimetric, nephelometric, fluorometric or luminometric) or radiometric measurement principles are particularly common. These methods permit the qualitative and quantitative detection of analytes in liquid samples, without having to provide additional separating steps. Clinically relevant parameters, such as the concentration or the activity of an analyte, are often determined by virtue of an aliquot of a bodily fluid of a patient being mixed, simultaneously or in succession, with one or more test reagents in the reaction vessel, as a result of which a biochemical reaction is started which brings about a measurable change in an optical property of the test mixture.

The measurement result is in turn forwarded from the measurement system to a storage unit and evaluated. Subsequently, the analysis apparatus supplies sample-specific measurement values to a user via an output medium, e.g. a monitor, a printer or a network connection.

The reaction vessels are often delivered to the various measurement systems on a circular transport wheel. A wheel of this kind is usually arranged with a perpendicular central axis in the automatic analysis apparatus and has, along its outer circumference, a large number of holders for reaction vessels. The reaction vessels are usually cylindrical and are oriented with their central axis parallel to that of the wheel. In this way, the reaction vessels can be inserted from above into the holders, moved to another location by means of rotation of the wheel and once again removed there.

Depending on how long the reaction vessels remain in the transport wheel, it may be necessary to protect the content of the reaction vessels from evaporation and external influences, e.g. dust or light. A lid is normally used for this purpose. However, in automated processing in an analysis apparatus, it is necessary that this lid can be automatically opened at any time and closed again, in order to add reagents or to remove sample liquid. The actuation of the lid should as far as possible be effected with already existing movements in the apparatus, such that no additional technical outlay is needed in respect of position determination and the actuation of the lid.

SUMMARY

The object of the invention is therefore to make available a closure system for a receiving position for a reaction vessel in an automatic analysis apparatus, wherein the closure system on the one hand permits automated opening and tight closure of the respective holder and on the other hand can be produced in what is a particularly simple and cost-effective manner from the technical point of view.

This object is achieved by the fact that the closure system comprises a lid which can be secured movably on a retainer element, wherein the lid closes an opening of the holder in a closed position and opens it in an open position. The closure system further comprises a restoring element, which is designed in such a way that, depending on the position of the lid, it exerts a restoring force in the direction of the open position or of the closed position.

This has the advantage of permitting a particularly simple and cost-effective construction of a closure system for reaction vessel holders, specifically in respect of the usually large number of holders, since the movement of the lid does not take place exclusively via an active control by e.g. electric motors, but instead involves the use of passive mechanical components. For this purpose, a restoring element is provided which, on the one hand, fixes the lid in a closed position, as a result of which it is possible, for example, to also obtain a pressure that contributes to the seal, but which, on the other hand, also fixes the lid in the open position, such that samples can be removed or reagents added without separate means for keeping the lid open. Moreover, the restoring element is designed such that, depending on the position of the lid, it restores to the open or closed position. This permits some degree of fuzziness with respect to the actuation: It is no longer necessary to bring the lid to an exact position completely by means of active components, and instead it suffices to bring the lid to a position starting from which it automatically reaches the desired open or closed position via the restoring element. This results in a high degree of flexibility in the construction of the actuation of the lid.

In a particularly advantageous embodiment, the open position of the lid is reached by rotating it about an axis by a predefined angle from the closed position. Here, the lid is secured on an arm, which is secured on a rotatable shaft. The axis about which the lid is movable is therefore preferably in the form of a shaft to which the lid is connected.

This permits a particularly advantageous design of the dual self-restoring function that has been described, in which a cam is in fact arranged on the shaft such that, in the closed position, it exerts a vertical force on the restoring element. A cam is a rounded projection that follows the rotation movement of the shaft. One or more restoring elements, e.g. springs, are by contrast fixed on the retainer element, such that they do not follow the rotation movement of the lid. The springs are arranged such that they act vertically on the cam, when the lid is closed. The spring force thus acts vertically on the cam. When the cam is inclined by rotation of the lid from the open position, the rounded projection of the cam is moved toward the spring, such that the force increases. The self-restoring effect is obtained as a result of this. The roundness of the cam determines the restoring properties, i.e. from which angle of rotation the restoring to the open position or the closed position takes place.

Only a single restoring element is needed that exerts the restoring force for both positions, i.e. open and closed.

Advantageously, the closure system also comprises a lever, which is mounted on at least one end of the shaft and extends radially on both sides of the axis. The lever permits actuation of the lid in a particularly simple manner. The lever in turn can be actuated, for example, by a bolt which is pressed against the end of the lever. The pressure causes a rotation movement of the shaft and therefore a rotation movement of the lid. As soon as the rotation has exceeded the angle of rotation at which the cam snaps over, i.e. which defines the limit between restoring to the open or closed position, the lid moves automatically to the respective other position, without having to be completely guided to the end position by the actuating bolt.

In an advantageous embodiment, the restoring element is designed as a flexural beam spring. A flexural beam spring of this kind consists of a straight beam, of which one end is fixed, and of which the other end floats free. The elasticity of the beam permits a movement of the free end which, however, always returns to the straight position again. The free end is arranged such that it exerts a restoring force on the cam. A design of this kind has many advantages: On the one hand, the extension of the flexural beam allows force to act across the rotating surface of the cam, which is necessary for the automatic restoration. On the other hand, the flexural beam can be produced directly, e.g. by injection molding. Separate attachment of metal springs or the like is not needed, which makes the production process easier.

Advantageously, the angle of the rotation between the open position and the closed position is 90°. The resulting symmetry simplifies the construction of the closure system. Moreover, the actuation of the lid mechanism is simplified, since a rotation of the described lever for example, or of an arm of the lever, through only 90° is needed. In this way, the actuation can only take place by a simple one-dimensional movement in one direction.

The lever is advantageously arranged in such a way that it forms an angle of 45° with a direction of insertion and removal of the holder. In this way, the opening and closing of the lid can be effected by a movement in the direction of insertion and removal. In this way, the opening and closing of the lid can be directly integrated in the access to the respective holder, e.g. by a suitably positioned bolt on an access device such as an automated pipet or a gripper arm.

The present invention further relates to a retaining device with a multiplicity of holders for reaction vessels, wherein a closure system according to the invention is arranged on each holder. The retaining device preferably comprises a retaining element for the closure system according to the invention. The retaining element can be produced, for example, by injection molding and can already contain parts of the closure system that are to be secured on the holders, e.g. the flexural beam springs and the bearings for the rotatable lid. This considerably simplifies production.

Moreover, the present invention also relates to an automatic analysis apparatus having a retaining device with a multiplicity of holders for reaction vessels, wherein a closure system according to the invention is arranged on each holder. The analysis apparatus also comprises an access device, e.g. a gripper for the reaction vessels and/or a pipetting device with a hollow needle, wherein the access device additionally has a bolt for actuating a closure system according to the invention.

The advantages achieved with the invention are in particular that, on account of the dual automatic restoration to an open position and a closed position in a closure system for reagent vessel receiving positions, a particularly simple actuation of the closure mechanism is achieved and, therefore, a cost-effective and technically simple closure of the receiving positions for reaction vessels in an automatic analysis apparatus is permitted.

BRIEF DESCRIPTION OF THE DRAWINGS

The invention is explained in more detail with reference to a drawing, in which:

FIG. 3 shows the closure system when actuated by a bolt in the open position, FIG. 4 shows a retaining element for a plurality of closure systems, FIG. 7 shows a rear view of the lid of the closure system.

Identical parts are provided with the same reference signs in all of the figures.

DETAILED DESCRIPTION

Figure 1:
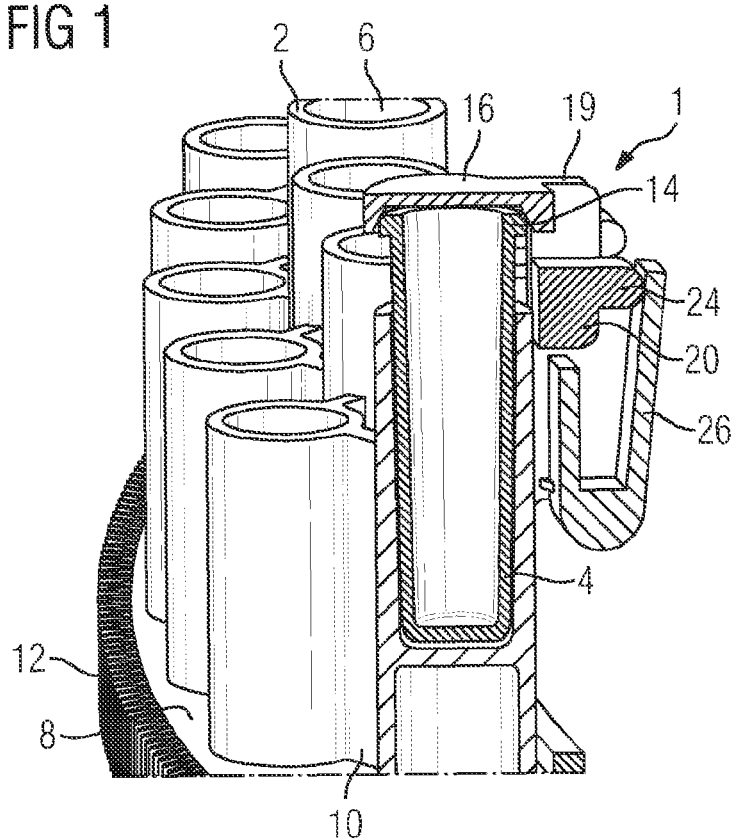
FIG. 1 shows a closure system for a holder for a reaction vessel on a segment of a transport wheel.

FIG. 1 shows, in cross section, a closure system 1 for a holder 2 for a reaction vessel 4 in an automatic analysis apparatus. Several holders 2, each with an opening 6, are arranged in two rows on a segment 8 of a transport wheel. For reasons of clarity, only one holder 2 is provided with a reference sign. The segment 8 is in the shape of an arc of a circle, wherein a first row of the holders 2 is arranged on a first arc of a circle. The other holders 2 are arranged on a second concentric arc of a circle with a larger radius, i.e. farther outward.

The holders 2 are designed substantially as hollow cylinders open at the top, wherein the inside is shaped slightly conically such that the direction of insertion and removal runs along the cylinder axis. The holders 2 arranged on the arc of a circle lying farther to the inside are higher than the holders 2 arranged farther to the outside. The holders 2 are connected in a zigzag formation by webs 10, which increase the stability.

The segment 8 is produced from a plastic by injection molding. A toothed ring 12 is arranged on the outer radius of the segment 8 and thus extends along the outside of the transport wheel, formed by the segments 8, for transporting reaction vessels. A toothed wheel (not shown in detail), which is moved via a drive, engages in this toothed ring. The drive is controlled by the control unit of the automatic analysis apparatus (not shown in detail), such that the control unit thus has control over the positioning of the transport wheel.

The cross section in FIG. 1 extends through one of the holders 2. A reaction vessel 4 is inserted into the opening 6 of the holder 2 shown in cross section. The reaction vessel 4 is designed as an upwardly open cone, of which the upper edge 14 is curved outward, and of which the outer shape is adapted to the inside of the holder 2, such that the reaction vessel 4 sits in a stable fashion in the holder 2. However, the reaction vessel 4 is not completely surrounded by the holder 2, but instead is higher than the holder 2, such that it protrudes from the opening 6.

The holder 2 shown in cross section in FIG. 1 is provided there as a single holder with a complete closure system 1. The latter comprises a lid 16, which is likewise shown in cross section and is adapted to the edge 14 of the cuvette, such that it closes the reaction vessel 4. The lid 16 is shown in a closed position in FIG. 1.

The lid 16 is secured on a shaft 20 via a right-angled retaining arm 19. A cam 24 is arranged on the shaft 20 such that, in the closed position shown, it exerts a vertical force on the restoring element 26.

The retainer element 18 (not shown here) comprises a flexural beam spring 26, which is substantially U-shaped, with the bend of the U being strengthened. The U shape has the effect that the spring excursion of the flexural beam spring 26 is lengthened. One end of the flexural beam spring 26 is connected fixedly to the retainer element 18, while the free end is arranged such that it can interact with the cam 24 via the inside of the U. If the lid 16 is opened only slightly, the cam 24 inclines, as a result of which the flexural beam spring 26 is deflected and thus exerts a restoring force in the direction of the closed position.

The retainer element 18 comprises a plurality of these flexural beam springs 26 which, for the remaining holders 2 of the segment 8, are arranged in the same way as for the described holder 2. The retainer element 18 and the flexural beam springs 26 are produced in one piece as a plastic injection-molded part. In FIG. 1, however, no lids 16 are arranged on the remaining holders 2.

Figure 2:
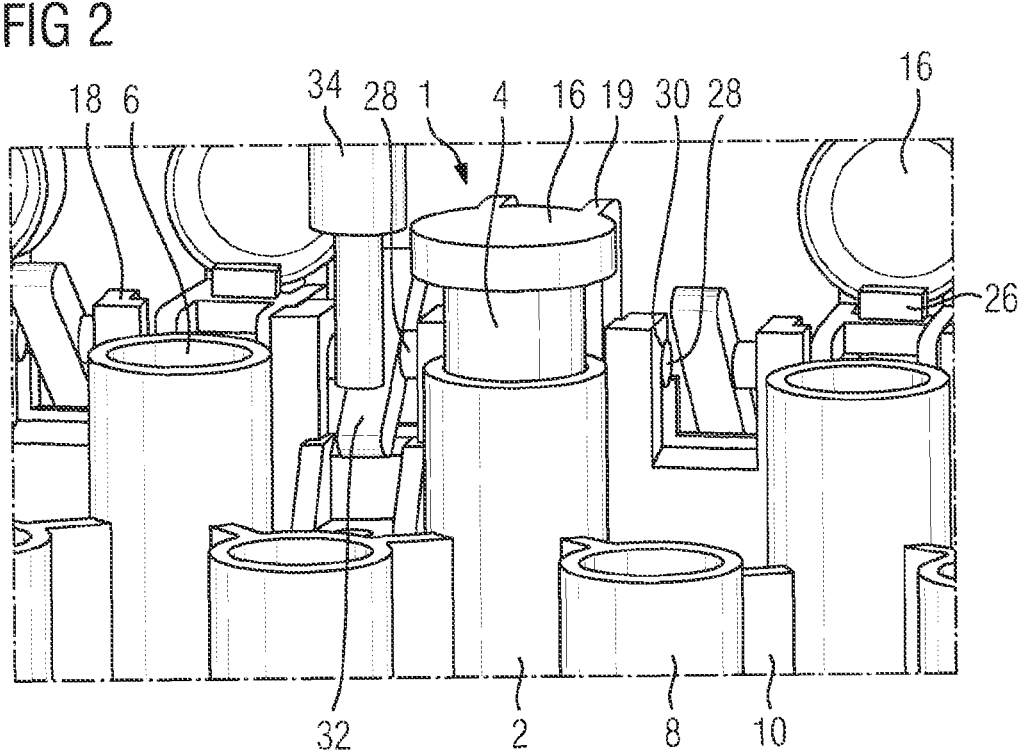
FIG. 2 shows the closure system when actuated by a bolt in the closed position.

FIG. 2 shows a view of the holder 2 with the lid 16 closed. To the right and left of the holder 2 shown in the middle, holders 2 are shown with open lids 16. In the open position, the lid 16 is tilted by 90° in the direction of the center point of the arc of a circle of the segment 8. Outwardly directed cylindrical webs 28 are arranged on the shaft 20, which is connected to the lid 16 via the retaining arm 19 and which forms the axis of rotation. The webs 28 are mounted rotatably in bearings 30 of the retainer element 18. The bearings 30 are open toward the center point of the arc of a circle of the segment 8, but the webs 28 are held in the bearings 30 by the force of the flexural beam spring 26.

The combination of FIG. 1 and FIG. 2 illustrates the dual restoring action of the flexural beam spring 26: In the closed position, a restoring action is exerted on the cam 24, as has already been described, which action additionally ensures, via the retaining arm 19, the necessary pressure of the lid 16 onto the edge 14 and thus safely closes the reaction vessel 4. When the lid 16 is opened by rotation in the axis of rotation counter to the restoring force, the flexural beam spring 26 yields. The maximum deflection of the flexural beam spring 26 is reached at a rotation through 45°, when the rounded tip of the cam 24 points in the direction of the center point of the arc of a circle of the segment 8.

If the rotation in the direction of the open position is continued, the force of the flexural beam spring 26 no longer acts in the direction of the closed position, but instead in the direction of the open position. No further force need be applied since, from this point onward, the lid 16 automatically tilts to the open position. The reverse closing process takes place analogously.

The lid 16 is actuated via a straight lever 32, which is secured centrally at the end of one of the webs 28, i.e. at one end of the shaft 20, and of which the arms extend on both sides of the axis of rotation. The lever 32 is arranged at 45° with respect to the direction of insertion and removal of the holder 2 and is oriented in such a way that an actuation of the lid 16 can take place from above. That is to say, one or other position of the lid 16 can respectively be reached by downward pressure on one of the lever arms. Here, the lever arm facing toward the center point of the arc of a circle of the segment 8, or facing away from the lid 16 in relation to the axis of rotation, lies at the top in the closed position.

The lid-opening mechanism is now actuated by the bolt 34 shown in FIG. 2. The bolt 34 can be secured, for example, directly on a gripper arm or a pipetting device of the automatic analysis apparatus, such that the actuation is integrated with the upward and downward movement that is already present anyway. For this purpose, the bolt 34 simply has to be brought over one of the two lever arms of the lever 32 and guided downward. A certain tolerance exists here in respect of the positioning, since the self-restoring action of the flexural beam spring 26 means that the position of the lid 16 is always either exactly open or closed. The bolt 34 therefore does not have to be brought so far down that the lever 32 reaches the position corresponding to the open or closed position of the lid.

FIG. 2 shows the bolt 34 after the actuation of the closure system 1 in the direction of the closed position.

FIG. 3 shows the device from FIG. 2 after the actuation of the closure system 1 in the direction of the open position. The bolt 34 was brought over the lever arm facing away from the lid 16 with respect to the axis of rotation and was guided downward.

FIG. 4 shows the retainer element 18 without lids 16 and before being placed on the segment 8. The retainer element 18 is produced as an injection-molded part from plastic and has bearings 30 arranged in the shape of an arc of a circle, and flexural beam springs 26 of the form described. Furthermore, it comprises three hollow cylindrical securing parts 36, which are arranged uniformly and serve to secure the retainer element 18 on the segment 8. The lids 16 can be secured on the retainer element 18 if necessary.

Figure 5:
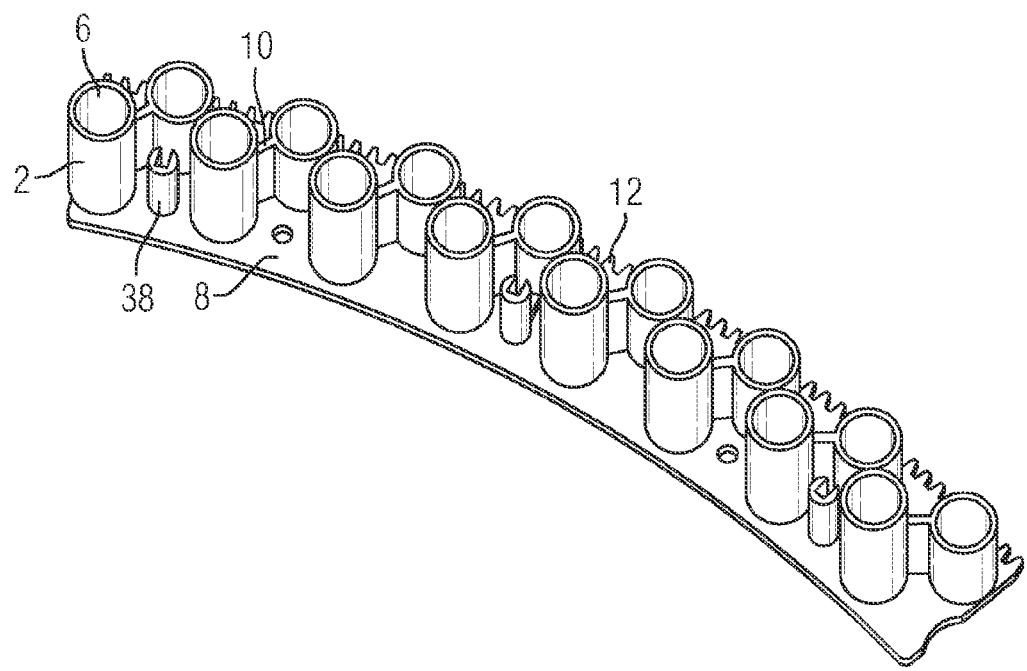
FIG. 5 shows the segment of the transport wheel.

FIG. 5 shows the already described segment 8 with the holders 2, without retainer element 18 and without closure system 1. The segment 8 has bolts 38 matching the securing parts 36 of the retainer element 18. The securing parts 36 are pushed over the bolts 38 and fixed, such that retainer element 18 and segment 8 are firmly connected.

Figure 6:
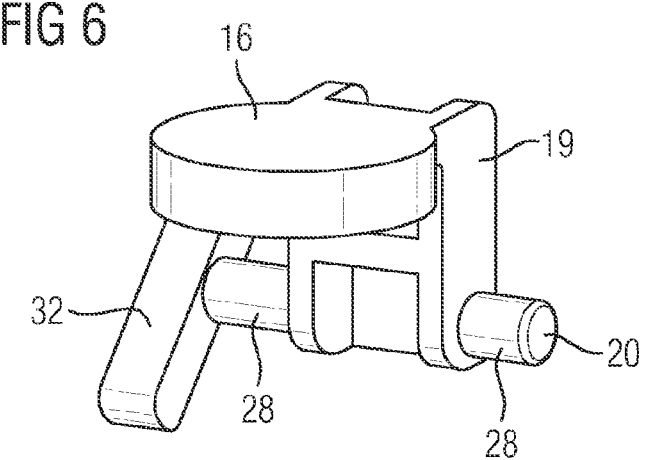
FIG. 6 shows a front view of the lid of the closure system.

FIG. 6 shows a front view of the part of the closure system 1 comprising the lid 16. It comprises the lid 16 and the two-part retaining arm 19. Furthermore, the part shown in FIG. 6 comprises the shaft 20 with the end webs 28 for the rotatable mounting, and the lever 32 for the actuation of the lid 16.

FIG. 7 shows a rear view of the part of the closure system 1 comprising the lid 16. In particular, the cam 24 on the shaft 20 can be clearly seen in this view.

LIST OF REFERENCE SIGNS 1 closure system
2 holder
4 reaction vessel
6 opening
8 segment
10 web
12 toothed ring
14 edge
16 lid
18 retainer element
19 retaining arm
20 shaft 24 cam
26 flexural beam spring
28 web
30 bearing
32 lever
34 bolt
36 securing part
38 bolt

The invention claimed is:

1. A closure system for a holder for a reaction vessel in an automatic analysis apparatus, the closure system comprising:
   a retainer element configured to connect fixedly to the holder and to support a lid;
   a shaft rotatably mounted to the retainer element;
   the lid secured movably to the retainer element via the shaft, wherein the lid rotates with the shaft and closes an opening of the holder in a closed position and opens the opening of the holder in an open position;
   a cam arranged on and rotating with the shaft; and
   a U-shaped restoring element comprising a U-shaped flexural beam spring configured to, depending on the position of the lid, exert a restoring force on the cam in the direction of the closed position or of the open position, the U-shaped restoring element having one end connected fixedly to the retainer element and a free end arranged to interact with the cam.

2. The closure system as claimed in claim 1, wherein the open position is reached by rotating the lid by an angle of 90° from the closed position.

3. The closure system as claimed in claim 1, wherein the cam is arranged on the shaft such that an initial opening of the lid from the closed position causes the restoring element to deflect and exert a restoring force in the direction of the closed position.

4. The closure system as claimed in claim 1, further comprising a lever mounted on at least one end of the shaft.

5. The closure system as claimed in claim 1, further comprising a retaining arm connecting the lid to the shaft.

6. The closure system as claimed in claim 5, further comprising a lever mounted on an end of the shaft, wherein the lever is arranged such that it forms an angle of 45° with a portion of the retaining arm.

7. A transport system for a reaction vessel in an automatic analysis apparatus, comprising:
   the closure system as claimed in claim 1;
   a segment of a transport wheel; and
   a holder configured to receive a reaction vessel, the holder having an opening and arranged in a row on the segment of the transport wheel; wherein:
   the retainer element is secured to the segment of the transport wheel; and
   the lid is positioned over the opening of the holder.

8. The transport system as claimed in claim 7, further comprising:
   a lever mounted on an end of the shaft; and
   a bolt for actuating the closure system, the bolt positioned over the lever and configured to move downward to engage the lever.

9. The transport system as claimed in claim 8, wherein the lever has a first arm and a second arm, and the bolt is configured to be positioned over and to engage the first arm to move the lid to the closed position and to be positioned over and to engage the second arm to move the lid to the open position.

10. The transport system as claimed in claim 7, wherein the segment of the transport wheel comprises a plurality of bolts, and the retainer element comprises a respective plurality of securing parts pushed over and secured to the plurality of bolts.

11. The transport system as claimed in claim 7, wherein the segment of the transport wheel comprises a toothed ring arranged on an outer radius of the segment of the transport wheel.

12. The closure system as claimed in claim 1, wherein the retainer element comprises a pair of bearings, and the shaft is rotatably mounted in the pair of bearings.

13. The closure system as claimed in claim 1, wherein the retainer element comprises a plurality of U-shaped restoring elements.

14. The closure system as claimed in claim 1, wherein the U-shaped restoring element comprises a bend having a thicker cross section than the free end and the one end connected fixedly to the retainer element.

15. The closure system as claimed in claim 1, wherein the retainer element and the U-shaped restoring element are formed in one piece as a plastic injection-molded part.

16. The closure system as claimed in claim 5, wherein the retaining arm has a right-angled shape.

17. A closure system for a holder for a reaction vessel in an automatic analysis apparatus, the closure system comprising:
   a lid configured to close an opening of the reaction vessel received in the holder;
   a shaft secured to the lid and configured to rotate the lid to and from a closed position and an open position;
   a right-angled retaining arm connecting the lid to the shaft;
   a lever mounted on an end of the shaft and rotating with the shaft;
   a cam arranged on the shaft and rotating with the shaft;
   a retainer element for supporting the lid and configured to connect fixedly to the holder, the retainer element comprising a pair of bearings to which the shaft is rotatably mounted; and
   a U-shaped flexural beam spring having one end connected fixedly to the retainer element and a free end arranged to interact with the cam.

* * * * *